United States Patent [19]
Kline

[11] Patent Number: 5,004,419
[45] Date of Patent: Apr. 2, 1991

[54] SCALERS FOR PERIODONTAL USE

[76] Inventor: Joseph M. Kline, 3501 N. Valley St., Arlington, Va. 22207

[21] Appl. No.: 470,785

[22] Filed: Jan. 26, 1990

Related U.S. Application Data

[63] Continuation-in-part of Ser. No. 348,416, May 8, 1989, abandoned.

[51] Int. Cl.$^5$ .............................................. A61C 17/00
[52] U.S. Cl. ..................................................... 433/143
[58] Field of Search ................................. 433/143, 144

[56] References Cited

U.S. PATENT DOCUMENTS

| | | | |
|---|---|---|---|
| 1,109,924 | 9/1914 | Hoffman et al. | 433/144 |
| 1,220,933 | 3/1917 | Bates | 433/144 |
| 1,497,749 | 6/1924 | Diack | 433/144 |
| 1,605,320 | 11/1926 | Bates | 433/144 |
| 1,605,321 | 11/1925 | Bates | 433/144 |
| 1,605,322 | 11/1925 | Bates | 433/144 |
| 2,002,245 | 5/1935 | McDaniel | 433/144 |
| 2,366,671 | 1/1945 | Montelius | 433/144 |

FOREIGN PATENT DOCUMENTS 1120992 10/1984 U.S.S.R. ............................... 433/143

OTHER PUBLICATIONS

GC American Curuettes, 2 pages ®1990 GC International 80127.
Advertisement, 1 page "You'll Be Hooked" GC International Corporation ®1990 1700-0013.
Feature/Benefit GC International, 2 pages ®1990 8012A.
Catlog "Brasseler USA", Inc. No. 3.
Catalog Nordent, 1982.
Catalog, Hu-Friedly, "Instruments for the Dental Hygienist".

Primary Examiner—Robert P. Swiatek
Assistant Examiner—Nicholas D. Lucchesi
Attorney, Agent, or Firm—Dowell & Dowell

[57] ABSTRACT

Periodontal and dental scalers and curettes for removing tartar and other debris from the outer surface of teeth and especially root areas and which incorporate blades which are carried by a handle with the blades including a concavely curved cutting edge which extends in a plane transverse to the elongated axis of the handle and which cutting edge is configured so as to conform to an arcuate segment of the outer surface of the root or crown portion of a tooth taken generally normal to the elongated axis of the tooth.

18 Claims, 2 Drawing Sheets

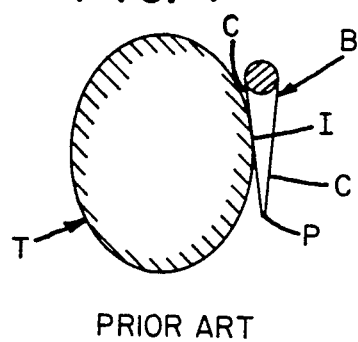
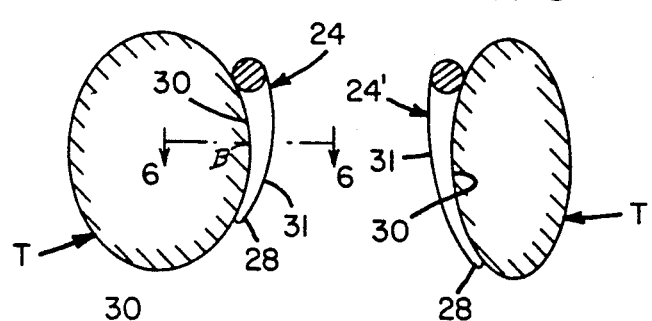
FIG. 1 PRIOR ART
FIG. 2
FIG. 3
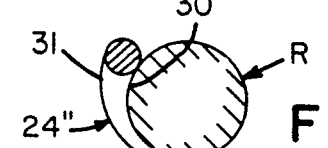
FIG. 4
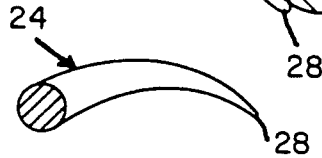
FIG. 8
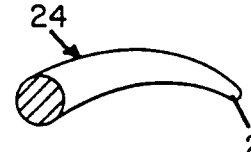
FIG. 9
FIG. 10
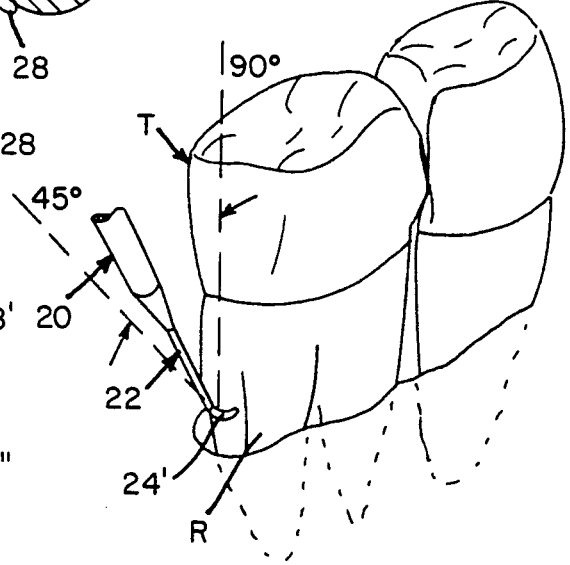
FIG. 5
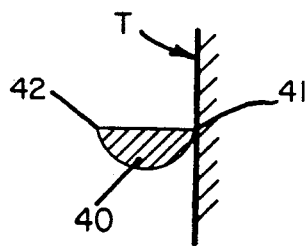
FIG. 7
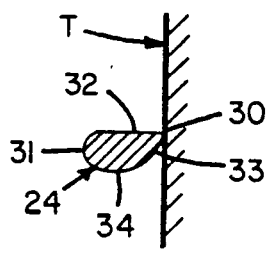
FIG. 6

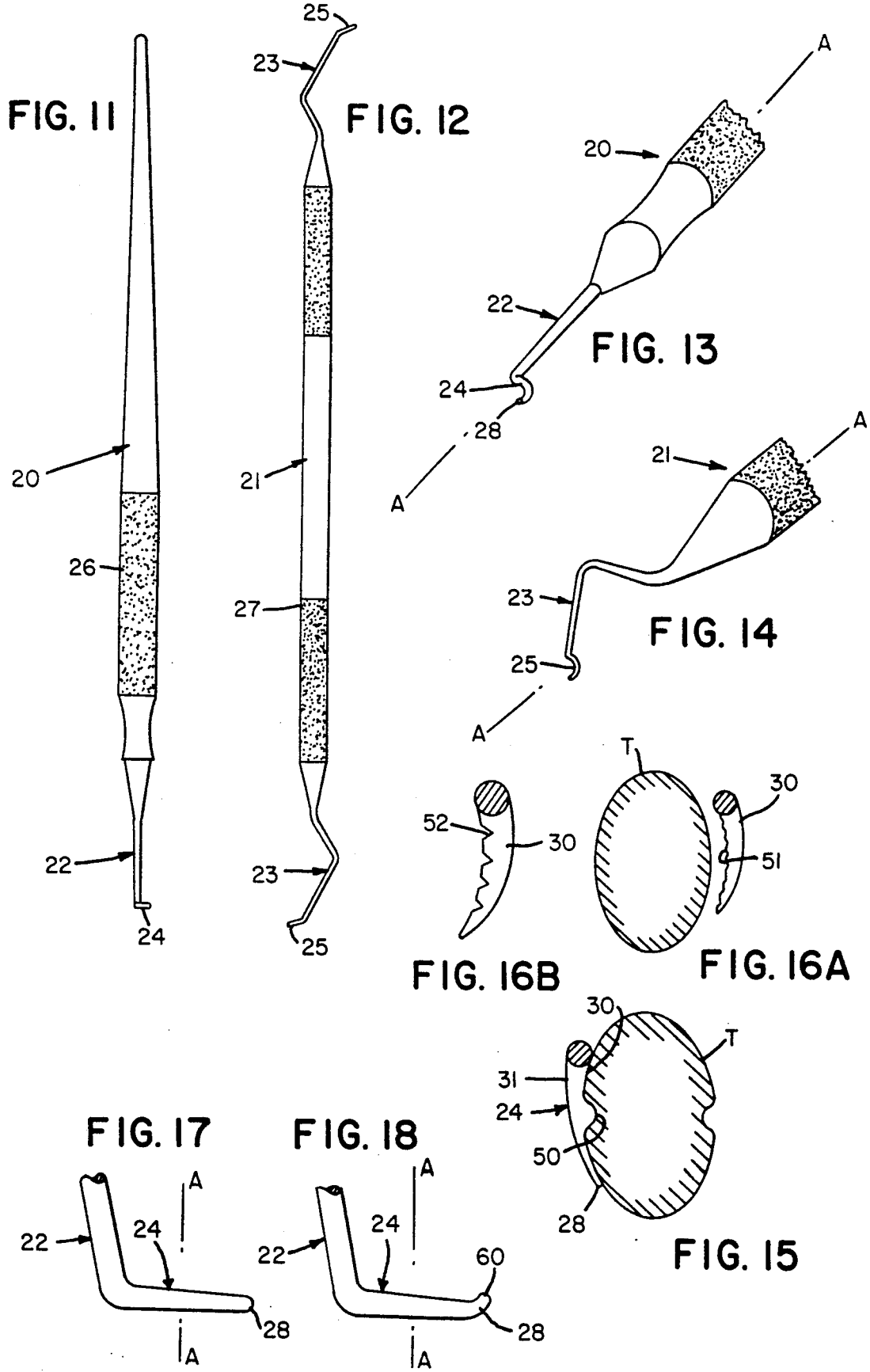

SCALERS FOR PERIODONTAL USE

CROSS REFERENCE TO RELATED APPLICATIONS

This application is a continuation-in-part application of Ser. No. 07/348,416 filed May 8, 1989 and entitled Scalers For Peridontal Use, now abandoned.

BACKGROUND OF THE INVENTION

1. Field of the Invention

This invention is generally directed to scalers and curettes which are utilized in periodontics and particularly to scalers and curettes having one or more blades which include inner concave cutting edges which are configured so as to conform with an arc segment portion of a root or crown area of a tooth with such segment being oriented generally perpendicularly to the elongated axis of the tooth. Further, the inner cutting edges are curved so as to create an arc which extends in a plane transverse to the elongated axis of the handle of the instrument so that the cutting edge conforms to the surface of a tooth when the handle is oriented between 45° and 90° with respect to the elongated axis of the tooth. It is preferred that approximately two to three millimeters or more of scaling edge will continuously engage the surface of the tooth depending upon the size of scaler or curette.

In the preferred embodiment of the present invention, the blades of the scalers or curettes include various sizes of blunted end portions, and the scalers incorporate an outer convex surface which is rounded so as not to adversely effect tissue adjacent the portion of the surface of the tooth which is being treated. However, in other embodiments, a pair of spaced generally parallel cutting edges will be provided along the blade of the scalers or curettes.

Although the scalers of the present invention are designed to incorporate blades which have cutting edges which continuously engage an arcuate segment of a tooth or the root of a tooth along a plane which is normal to the elongated axis of the tooth when the handle of the instrument is oriented in a conventional manner at angles of between 45° to 90° with respect to the elongated axis of a tooth, the specific curvature of the blades will be varied depending upon the circumference of a tooth and the size of root being scaled, planed or curettaged. The smallest working ends have a greater degree of curvature and are for use on small root areas such as the lower anterior and upper laterals and bifurcated first bicuspids and upper first molars. The medium or intermediately curved blades are for use on centrals, cuspid and bicuspids, and the least curved or large blades are for use on molars and other large surface areas.

The tip portion of the blades of the scalers in some instances may be curved uniformally with the cutting edges so that the tip will not gouge into tissue surrounding a tooth surface or root being scaled. In addition, the tips will preferably be provided in various sizes. The finest point tip will be utilized for finer bifurcations and narrower spaces; the intermediate blunted tip being utilized for small bifurcations between roots; and the larger rounded tips being utilized in larger areas of scaling between the two roots of lower first molars.

The scalers or curettes of the present invention will generally be designed to provide for both left and right hand curvature with a blade being disposed to the right along one end of the handle of the instrument for scaling one side of a tooth with the blade on the opposite end being oppositely curved so that the same instrument may be utilized for scaling the opposite side of the tooth.

In other separate embodiments, the concave cutting edge of the scaler blades may include one or more projections intermediate their length for scaling slight indentations along the surface areas of some teeth; a saw-toothed like edged surface for scraping hard built-up areas of tartar; or a notched surface for working in roughened or irregular surface locations and also hard built-up areas of tartar. In a further embodiment, the tip of the blade will be curved slightly upwardly to create a spoon effect for scaling all bifurcations and root indentations.

2. History of the Related Art

Periodontal treatment requires the use of a scaler or a curette instrument to remove off the tartar and debris which forms or accumulates on the root surfaces and periodontal pockets. This material acts like a foreign body much as a splinter would in a finger. By removing this material, the tissue adjacent the tooth will become less inflamed and will heal against the root surface or crown portion of the tooth. It has been found that regular scaling promotes healthy teeth and gums and results in many adults being able to retain their natural teeth.

Conventional scalers and curettes have relatively straight scraping or cutting blade portions in relation to the natural curvature of a tooth and also terminate with sharp tips. As conventional scalers and curettes are provided with a straight blade configuration when compared with the cross sectional configuration of a tooth, only a small portion of the working end of the curette or scaler engages a tooth at any one time. Generally, not more than approximately one-tenth of a millimeter of the cutting edge of the scaler or curette actually engages a tooth or the root of the tooth during scaling. Because of this, it is possible to gouge the surface of the tooth along a given portion of the tooth surface especially after repeated scalings as uniform scaling of the surface of the tooth is not provided for.

There have been several scalers designed to more closely conform to the surface characteristics or shapes of teeth. In U.S. Pat. No. 1,220,933 to Bates, dental scalers are disclosed which incorporate blades which are concave so as to conform to the convexity of a root of a tooth. However, the cutting blades are always formed so as to be aligned with the axis of the handles of the instruments. Thus, such scalers had a curvature which is similar to most of today's conventional scalers wherein the blades are curved upwardly toward the axis of the handles of the instruments. In this manner, the curved blades could be used to lift debris from between the roots of teeth and the surrounding gum tissue. However, due to the orientation of the blades and the handles only a small portion of a tooth could be scaled or curettaged with each vertical movement of the blades. Further, with the Bates blade structure, the pointed tip would gouge the surrounding tissue of patient causing pain.

In U.S. Pat. No. 1,605,320 to Bates, a similar scaler or curette is disclosed which includes a blade having cutting edges which are again curved toward the axis of the instrument handle except that a somewhat spiral configuration is given to the cutting edges. With such an instrument, the cutting blades can only be used to scrape larger surface areas of a tooth by rotating the instrument handle into a very angular relationship with respect to the elongated axis of the tooth thereby limiting the efficiency of the depth of treatment relative to a patient's gum tissue. Deeper scaling or curettaging requires the cutting edge to be progressively more vertically oriented and thus results in a smaller surface area being scaled or curettaged with each vertical lifting of the cutting blades relative to a patient's teeth.

Additional prior art references includes U.S. Pat. Nos. 1,605,321 and 1,605,322 to Bates, 2,366,671 to Montelius, 1,497,749 to Diack and 2,002,245 to McDaniel.

In addition to the foregoing, with conventional scalers and curettes, the tips of the blades extend outwardly relative to the surface of the tooth and therefore lacerates or cuts the surrounding tissue when the scaler or curette is being moved vertically relative to the surface of the tooth during scaling. In normal use, a scaler or curette is urged down to the root area of the gingival attachment to the tooth with the scraping or scaling being accomplished by raising or drawing the blade of the instrument vertically toward the top of the tooth. In order to provide a proper angle of contact of the cutting edge with the surface of the tooth, curettes are generally provided with a hooked end portion with the end portion being utilized to trap material being scraped and lift the material as the instrument is drawn upwardly toward the top of the tooth. Unfortunately, the curvature provided on conventional curettes and scalers does not provide for conforming the cutting edge of the scaler with the surface of the tooth. Therefore, only a small portion of the tooth is scraped with each movement of the scaler or curette.

A further problem inherent in conventional scalers and curettes is that they are normally provided with a cutting edge on opposite edges of the blade or working end of the scaler. Therefore, with the scaler engaging the surface of a tooth, there is a sharp cutting edge which extends outwardly into the surrounding tissue. As the scaler or curette is moved, the surrounding tissue is lacerated thereby causing trauma of the local tissue area and also inflicting pain upon the patient.

SUMMARY OF THE INVENTION

This invention is directed to scalers and curettes which have at least one working end or blade which is mounted to an elongated handle with the blade having a cutting edge portion which is arcuately shaped so as to conform to an arcuate segment of the surface of the tooth, when viewed in cross section in a plane taken normal to the elongated axis of the tooth, with the tip of the blade, in some embodiments, generally following the same contour. The cutting edge is also oriented so as to extend in a plane which is generally transverse to the elongated axis of the handle so that a significant portion of the cutting edge is in continuous contact with the surface of a tooth during scaling and currettaging even in deep root areas. Generally, the transverse arc of the cutting blades will assure proper tooth contact when the handle of the instrument is oriented between 45° to 90° with respect to the elongated axis of a tooth with most dental scalers being oriented down to 70° with respect to the tooth axis when in use. In the preferred embodiment for scalers, the outer convex portion of the working end or blade which is opposite the cutting edge portion is rounded so as not to adversely affect surrounding inflamed tissue as the scaler is being utilized.

Further, in both scalers and curettes the tip of the blade is generally blunt so as to not lacerate surrounding tissue as the tip is moved relative to the surface of a tooth.

In some embodiments of the present invention, the blade portion may consist of a pair of cutting edges which are spaced relative to one another of which arc edge contacts the surface of the tooth.

The scalers or curettes of the present invention will generally include a pair of blade portions with one blade being oriented in a first direction on one end of the instrument handle and with the opposite blade being oppositely oriented on the opposite end of the handle so that a single scaler or curette may be utilized on opposite surfaces of a given root or tooth area (mesial or distal).

As the scalers of the present invention are designed to incorporate cutting edges which are curved so as to be complimentary to a portion of the surface of a tooth and as the cutting edges are also oriented generally transverse to the elongated axis of the instrument handle, the degree of curvature of the cutting blades will depend upon the size of root or tooth area which is to be scaled, planed or curettaged. For molar and other larger surface areas, the degree of curvature will be less than for scalers which are designed to be utilized for scraping small root areas, such as the bottom of deep pockets, and lower anteriors and upper laterals. Other scalers or curettes having an intermediate degree of curvature will be utilized for areas such as central areas and bicuspids. It is envisioned that the cutting blade portion of the scalers of the present invention will generally have a degree of curvature sufficient enough to engage at least two to three millimeters or more of surface area of the tooth with each movement of the scaler or curette.

In an alternate embodiment, the cutting edge of the blade portions of the scalers or curettes of the invention will include a projection which will permit scaling in depressions or indentations found in the surface area of some teeth, and in another embodiment the tip of the blades will be curved upwardly to create a spoon effect for scaling bifurcations and root indentations.

It is a primary object of the present invention to provide curettes and scalers which have cutting blades which are arcuately curved so as to be complimentary in configuration to an arcuate segment of the surface of a tooth, when viewed in cross section through a plane normal to the elongated axis of the tooth and wherein the cutting edge of the blade extends transverse to the elongated axis of the handle of the instrument so as to assure proper tooth surface contact of the curved cutting edges when the instrument handle is oriented between 45° to 90° with respect to the elongated axis of the tooth, so that a wider and deeper area of tooth or root surface may be scaled, planed or curettaged at one time.

It is another object of the present invention to provide curettes or scalers which incorporate concave cutting blade portions which are generally complimentary to the outer surface configuration of a tooth or root area and which include outer end or tip portions which extend in proximate relationship to the surface of the tooth during scaling or curettaging.

It is a further object of the present invention to provide scalers and curettes for scaling, planing and curettaging teeth wherein the tip of the blade or working end is slightly blunted or rounded so as to thereby reduce the possibility of trauma or laceration to the issue area surrounding a tooth and further to promote scaling in pockets and areas between the roots of teeth.

It is also an object of the present invention to provide scalers for scaling and planing teeth which, in a preferred embodiment, include a blade or working end which includes a concave cutting edge and a rounded convex outer portion opposite the cutting edge so that the outer portion which engages the tissue area adjacent the teeth is not lacerated during patient treatment.

It is yet a further object of the present invention to provide scalers and curettes which have blade portions which are complimentary to an arcuate segment of the surface portion of a tooth when viewed in cross section through a plane normal to the elongated axis of the tooth with the blades having varying arcuate configurations so that different blades may be utilized for different tooth surface areas.

It is also an object of the present invention to provide scalers or curettes having arcuate blades wherein a portion of the arcuate cutting edge of the blades may include one or more projections intermediate the length of the blade which projections may be utilized for scaling indentations in the surface area of some teeth or wherein the cutting edge will be defined having a saw tooth surface or spaced notches for scaling special areas or hardened tartar.

It is yet another object of the present invention to provide scalers or curettes wherein the tip portion of the cutting blade is curved upwardly to create a "spoon-like" configuration for scaling root indentations.

BRIEF DESCRIPTION OF THE DRAWINGS

FIG. 1 is a cross sectional illustrational view of a prior art cutting blade of a conventional scaler or curette showing the generally linear contact of the cutting blade relative to the surface of a tooth.

FIG. 2 is a cross sectional illustration showing a cutting blade of the present invention as it is arcuately configured so as to engage a continuous arcuate segment of the outer surface of a tooth.

FIG. 3 is a cross sectional illustrational view showing the cutting blade of the present invention of a size to scale a larger tooth than the cutting blade shown in FIG. 2.

FIG. 4 is a cross sectional illustrational view of the cutting blade of a scaler of the present invention wherein the configuration is more arcuate than that of the embodiments of FIGS. 2 and 3 and wherein the cutting blade is designed to be utilized on smaller root or tooth surface areas.

FIG. 5 is an illustrational view showing the cutting blade portion of the curette or scaler of the present invention as it is utilized to scrape a deep pocket portion of a root of a tooth.

FIG. 6 is a cross sectional illustrational view along lines 6—6 of FIG. 2 of the preferred configuration for the cutting edge and blade portion of the scalers of the present invention showing the cutting edge engaging the surface of a tooth.

FIG. 7 is an alternate embodiment of cross section showing a pair of opposing cutting edges on a cutting blade of the scalers and curettes of the present invention.

FIG. 8 is an enlarged perspective view showing the cutting blade portion of the present invention incorporating a small tip portion.

FIG. 9 is an enlarged perspective view of the cutting blade of the present invention incorporating a tip which is blunted with respect to the tip of FIG. 8 for cleaning different surface areas.

FIG. 10 is an enlarged perspective view of a third configuration of cutting blade having a blunted end portion for cleaning between roots of teeth.

FIG. 11 is a front plan view of a scaler incorporating the blade elements of the present invention.

FIG. 12 is a side elevational view of a curette incorporating the blade elements of the present invention.

FIG. 13 is an enlarged perspective view of the cutting blade portion of the scaler of FIG. 11 showing the transverse orientation of the cutting blade with respect to the axis of the handle.

FIG. 14 is an enlarged perspective view of the cutting blade portion of the curette of FIG. 12 showing the transverse orientation of the cutting blade with respect to the axis of the handle.

FIG. 15 is a cross sectional illustrational view showing an alternate embodiment for the cutting blade of the present invention incorporating a projection along the cutting edge portion of the blade for engaging indentations in the surface of a tooth.

FIGS. 16A and 16B are cross sectional illustrations of two additional embodiments of specialized cutting edges for scraping built-up tartar or engaging irregular surface areas of a tooth.

FIG. 17 is an elevational view of the cutting blade of the scaler of FIG. 11 again showing the orientation with respect to the axis of the handle.

FIG. 18 is an elevational view of an alternate embodiment of cutting blade for the scaler of FIG. 11 also showing the orientation with respect to the axis of the handle.

DESCRIPTION OF THE PREFERRED EMBODIMENT

With continued reference to the drawings, conventional curettes and scalers incorporate cutting blades which have cutting edges which are linearly oriented with respect to the surface of a tooth. As shown in FIG. 1, the cutting blades "B" incorporate straight cutting edges "C" which are formed on either side of the blade. The cutting edge "C" which contacts the tooth "T" makes contact at a single point of intersection "I" so that only a small portion of the surface of the tooth is contacted during scaling, planing or curettaging. Generally, the blade portion of conventional scalers or curettes will be arcuate or hooked so that the tip or point "P" of the blade is elevated with respect to the central portion of the blade. Due to the configuration of such conventional scalers and curettes, the point of the blade "P" extends outwardly with respect to the surface of a tooth during scaling or curettaging thereby allowing the point to lacerate surrounding gum tissue. Further, due to the opposing cutting edges "C", the outer cutting edge will also lacerate surrounding tissue during scaling and curettaging. Therefore, conventional scalers not only do not conform the blade with the surface of a tooth but also have the inherent structural disadvantages of causing possible trauma to the tissue area surrounding a tooth being treated.

With specific reference to FIGS. 11-14, the present invention may be embodied either in a scaler 20 or a curette 21. The scalers and curettes 20 and 21 include working end portions 22 and 23 respectively with the working end portion 22 of the scaler 20 generally being more linearly oriented than the angled configuration shown with respect to the working end portion 23 of the curette. Although the curette is shown as having opposing or oppositely oriented working end portions 23, the scaler 20 may also be provided with oppositely oriented working ends 22. Generally, the working end portions on either end of the scaler will be oppositely oriented so that the cutting blade portions 24 and 25 of the scalers or curettes will be oppositely oriented so that the cutting blades may be utilized for opposing areas of a tooth surface. The handles 26 and 27 of the scalers and curettes of the present invention may have different forms or shapes so as to facilitate gripping of the instruments during use. The shapes shown in the drawings are purely illustrative of two forms for such handles.

With respect to FIGS. 13 and 14, it is noted that the working ends 22 and 23 of the scalers and curettes include arcuately shaped cutting blades 24 and 25. Further, the outer end portions or tips 28 of the cutting blades 24 and 25 are slightly blunted as is illustrated for reasons which will be discussed in greater detail hereinafter.

As the configuration of the cutting blades 24 and 25 of the scalers and curettes of the present invention are identical, with the exception that curettes include spaced cutting edges, the remaining portion of the description of the preferred embodiment will be directed to the different modifications or configurations for the cutting blade 24 of the scaler 20, it being remembered that the description of the cutting blade portion 25 of curette 21 would be the same with the exception of the round convex portion of the cutting blade of the scalers as discussed hereinafter.

With specific reference to FIGS. 2-4, the configuration of the cutting blades of the invention are shown as they are designed to conform to an arcuate segment of the surface of a tooth or root of a tooth when viewed in cross section through a plane normal to the elongated axis of the tooth. The tooth is designated as "T" with the root being designated as "R" as noted in the three drawing figures. The degree of arc of the illustrated cutting blades varies depending upon the size and shape of the tooth or root which is to be scaled or curettaged. In FIG. 4, the blade portion 24" is the most arcuately configured blade shown in the drawings and is designed to be complimentary to the generally round shape of the small root areas of teeth so as to enable the blade to be used at the bottom of deep root pockets. In FIG. 3, the blade portion 24' has the least arcuate configuration and is designed for use on molar and other large surface areas. In FIG. 2, an intermediately configured or arcuately shaped blade 24 is disclosed which is designed to be used on teeth such as the central teeth and bicuspids.

It should also be noted that the cutting blades of the present invention are arcuately curved in a plane which is transverse to the elongated axis A—A of the handle of the scaler or curette. In some instances the blades will be generally aligned about the axis of the handle as shown in FIG. 14 and in other instances the blades will be spaced from the axis A—A, as shown in FIG. 13. In each case however, and as also illustrated in FIGS. 16 and 17, the concave curvature of the cutting edge of the blades is such that the cutting edge will conform to the curvature of the tooth, when view in cross-section in a plane normal to the elongated axis of the tooth, with the handle of the instrument being oriented between 45° to 90° with respect to the elongated axis of a tooth (see FIG. 5). Preferably, the instrument will be held at angles closer to 70° with respect to the elongated axis of a tooth. In practice, the instrument assures a more parallel or 90° orientation with respect to the front teeth with lesser angle of orientation being required with respect to the back teeth or molars.

Each of the cutting blades 24, 24', and 24" includes an innermost concave cutting edge 30 which is designed and configured so as to engage the surface of the tooth along a distance of two to three millimeters or more so that at least two or more millimeters of surface of the tooth, and preferably more than two millimeters on larger teeth, is contacted by the cutting edge 30 during the use of the scaler or curette. Further, the tip 28 of each of the cutting blades follows the general curvature of the cutting edge 30 so that the tip portions 28 extend adjacent or proximate to the surface of the tooth or root of the tooth during scaling or curettaging. In this manner, trauma to the surrounding tissue is effectively eliminated as the tip portion 28 is moved relative to the surface of the tooth or root of the tooth.

To further reduce laceration and resulting trauma in the tissue surrounding a tooth, the cutting blades 24, 24' and 24" of the scalers only have an outer convex surface portion 31 which is rounded so that the cutting blade will not lacerate the tissue adjacent a tooth as the cutting blade is moved relative to the surface of the tooth or the root of the tooth.

With respect to FIGS. 2 and 3, it is noted that the direction of curvature of the cutting blades of the present invention may be reversed as was discussed above with respect to the end portions 23 of the curette 21 so that a single instrument may be utilized to treat opposing surfaces of a tooth, as is illustrated.

With respect to FIG. 6, the preferred cross sectional configuration of the cutting blades 24, 24' and 24" for scalers are illustrated in greater detail. As shown, the inner concave cutting edge 30 is sharply defined and engages the tooth with the outer convex portion of the cutting blade 31 being rounded so as to pass through surrounding tissue without causing lacerations or trauma to the tissue. The cutting edge 30 is generally defined by intersecting side wall portions 32 and 33 which are joined by an arcuate wall portion 34 which defines the outer portion 31 of the cutting blade.

In some scaler embodiments of the present invention and for the curettes, the cutting blade will be formed having a pair of cutting edges. With respect to FIG. 7, a second embodiment of cutting blade 40 is disclosed having an inner concave cutting edge 41 which is designed to engage the surface of a tooth or the root of a tooth and outwardly oriented cutting edge 42 which extends into the tissue area surrounding the tooth as is the case with conventional curettes and scalers.

A further advantage of the present invention is that the tip portion 28 of the cutting blades 24 are slightly blunted or rounded to further prevent the possibility of tissue damage during the use of an instrument incorporating the blade configuration. In order to further maximize the utility of the instruments incorporating the blade configuration of the present invention, the tip portions 28 may be modified with respect to one another so that different advantages may be obtained for cleaning areas adjacent the roots of teeth. In FIG. 8, the cutting blade 24 incorporates a tip portion 28 which is slightly blunted. This slightly blunted tip portion is designed to be utilized for scaling or curettaging in narrow spaces and fine areas along the roots of a tooth. In FIG. 9, the tip portion 28' of the cutting blade 24 is shown as being more rounded than the tip portion 28 of FIG. 8. This intermediate type of blunt tip is designed to be utilized for small bifurcations created between the roots of teeth. In FIG. 10, the tip portion 28" of the cutting blade 24 shown as being rounded and is designed for scaling or cleaning areas between the roots of a tooth.

From the foregoing it is seen that various modifications may be made to the cutting blades 24 of the present invention so that the utility of instruments incorporating the features of the present invention may be widely expanded. However, it is the configuration of the cutting edge 30 of the present invention which allows scaling or curettaging to be performed over greater portions of the surface of a tooth or the root of a tooth thereby both facilitating uniform cleaning of the surface area and reducing the risk of gouging of any portion of the surface of a tooth during scaling, cleaning or curettaging.

The cutting blades of the present invention are preferably formed from a rust resistant high tensile strength steel alloy having a high degree of shore hardness which is able to retain a sharp cutting edge. In use of the instruments of the present invention, and with respect to FIG. 5 of the drawings, the scaler 20 is inserted intermediate the gum tissue and the surface of a tooth root with the cutting edge 30 engaging the surface of the tooth. With the cutting edge engaging the surface of the tooth the scaler 20 is raised toward the top of the tooth urging the cutting edge 30 along the surface of the tooth to thereby remove tarter and other debris from the root and crown portion of the tooth. Depending upon the exact shape and configuration of the root or tooth surface area, a selection will be made with respect to the exact arcuate configuration of cutting blade 24 to utilize for any scaling, cleaning or curettaging. Further, the size of the tip will also be selectively chosen depending upon the exact nature of the cleaning which is to be accomplished.

A further modification of the invention is shown in FIG. 15 of the drawings. In some instances, the surface of a tooth may include slight indentations which would not conform to the continuous arcuate curvature of the cutting blades of the present invention. In order to provide for the effective cleaning of such areas, the present invention may be modified to incorporate one or more slight projections 50 along the cutting edge portion 30 of the cutting blade 24 which corresponds to the cutting edge 41 of the curette or double edged scaler 40. Generally, such projections are slightly rounded as is illustrated and are generally not more than approximately a millimeter in length. The remaining portion of the cutting blade in this modification should not interfere with the projection and may assume any of the varied structures and curvatures as was discussed above with respect to the preferred embodiment of the invention. Other variations in cutting blades are shown in FIGS. 16A-B. In FIG. 16A, the cutting edge 30 of the blade 24 is shown as including a saw-tooth like structure having a plurality of closely spaced generally V-shaped teeth 51. This type of blade may be used to scrape hardened built-up areas of tartar on the surface of the teeth. In FIG. 16B, the cutting edge 30 is shown as being defined by a series of generally V-shaped notches 52. This type of cutting edge may be used along irregular surface areas of teeth and roots.

Another embodiment of the invention is shown in FIG. 18. In this embodiment, the tip portion 60 of the blade 24 is raised or curves upwardly so as to create a "spoon-like" configuration for scraping bifurcations and root indentations more thoroughly. Generally, the upward curvature need not exceed two-tenths to three-tenths of a millimeter. The cutting edge 30 of the blade extends along the upwardly curved tip portion 60. The tip 28 of the cutting blade when not curved upwardly would appear as is shown in FIG. 17.

In all embodiments, it is also possible to curve the length of the blade sligthly upwardly toward the axis of the handle as is the case with conventional curettes and scalers, however, the primary arcuate curvature of the cutting edges to conform to the surface of a tooth when the handle is raised in scaling or curettaging position must be maintained.

It should be further noted that each of the embodiments of the present invention may also be used on ultrasonic and vibratory type dental instruments.

I claim:

1. In a dental instrument of the type including a scaler and a curette having a handle having a central elongated axis and at least one working end portion for scaling the surface of teeth wherein the surface of the teeth have a generally arcuate configuration in a plane generally normal to the elongated axis of the teeth the improvement comprising, the working end having a cutting blade extending therefrom, said working end extending longitudinally outwardly with respect to the central elongated axis of the handle said cutting blade having an inner concave portion and an outer convex portion, said inner concave portion including a cutting edge which is arcuately shaped in a plane oriented transverse to the elongated axis of the handle so as to be complimentary to said arcuate configuration of a tooth when said central elongated axis of said handle is oriented at between 45° to 90° with respect to the elongated axis of a tooth, whereby said cutting edge portion will continuously contact an arcuate segment of the surface of the tooth during scaling.

2. The dental instrument of claim 1 in which said cutting blade includes an outer tip portion, said outer tip portion being slightly blunted, said outer tip portion extending from said cutting edge so as to be proximate to the surface of the tooth when said cutting edge is engaged with the surface of a tooth.

3. The dental instrument of claim 2 in which said cutting edge includes a projection formed intermediate the length thereof, said projection extending outwardly with respect to the inner concave portion of the cutting blade.

4. The dental instrument of claim 2 in which said arcuately shaped cutting edge is at least two millimeters in length.

5. The dental instrument of claim 2 in which said outer tip portion includes an outermost end which curves upwardly relative to a plane defined by said inner concave portion of said cutting blade.

6. The dental instrument of claim 5 in which said outermost end of said outer tip portion is approximately two-tenths to three-tenths of a millimeter in length.

7. The dental instrument of claim 1 in which said cutting edge includes at least one projection formed intermediate the length thereof, said projection extending outwardly with respect to the inner concave portion of the cutting blade.

8. The dental instrument of claim 7 in which said cutting edge is of a saw-toothed configuration having a plurality of generally V-shaped projections.

9. The dental instrument of claim 1 in which said arcuate cutting edge is at least two millimeters in length.

10. The dental instrument of claim 1 in which said cutting blade includes a tip portion, said tip portion includes an outermost end which curves upwardly with respect to a plane defined by said inner concave portion of said cutting blade.

11. The dental instrument of claim 10 in which said outermost end is approximately two-tenths to three-tenths of a millimeter in length.

12. The dental instrument of claim 1 in which said cutting edge of said cutting blade includes a plurality of spaced notches formed therein.

13. In a scaler having a handle and at least one working end portion for scaling the surface of teeth wherein the surface of the teeth have a generally arcuate configuration the improvement comprising, the working end having a cutting blade extending therefrom, said working end extending longitudinally outwardly with respect to the central elongated axis of the handle said cutting blade having an inner concave portion and an outer convex portion, said outer convex portion of said cutting blade being rounded, said inner concave portion including a cutting edge which is arcuately shaped in a plane oriented transversely with respect to the central elongated axis of the handle so as to be complimentary to the arcuate surface of a tooth, whereby said cutting edge portion will continuously contact an arcuate segment of the surface of the tooth during scaling.

14. The scaler or curette of claim 13 in which said cutting edge includes a projection formed intermediate the length thereof.

15. The scaler of claim 14 in which said cutting edge is of a saw-toothed configuration.

16. The scaler of claim 13 in which said cutting edge is at least two millimeters in length.

17. The scaler of claim 13 in which said cutting blade includes a tip portion, said tip portion including an outermost end which is curved upwardly with respect to a plane defined by said inner concave portion of said cutting blade.

18. The scaler of claim 13 in which said cutting edge includes a plurality of spaced notches therein.

* * * * *